United States Patent
Eghbalnia et al.

(10) Patent No.: US 8,512,676 B1
(45) Date of Patent: Aug. 20, 2013

(54) DETECTION OF RATE CHANGES IN SYSTEMATIC OSCILLATIONS OF METABOLIC ATHWAYS BY MONITORING ISOTOPE RATIOS

(75) Inventors: Hamid R. Eghbalnia, Cincinnati, OH (US); Mark E. Cook, Madison, WI (US); Warren Paul Porter, Fitchburg, WI (US); Daniel Elmer Butz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/414,061

(22) Filed: Mar. 7, 2012

(51) Int. Cl.
*A61K 51/00* (2006.01)

(52) U.S. Cl.
USPC .................................. 424/1.81; 600/532

(58) Field of Classification Search
USPC .................................. 424/1.81; 600/532
See application file for complete search history.

(56) References Cited

U.S. PATENT DOCUMENTS

| | | | | |
|---|---|---|---|---|
| 5,912,178 | A * | 6/1999 | Porter et al. | 436/55 |
| 7,465,276 | B2 * | 12/2008 | Assadi-Porter et al. | 600/532 |
| 8,026,049 | B2 * | 9/2011 | Assadi-Porter et al. | 435/5 |
| 2002/0007249 | A1 * | 1/2002 | Cranley et al. | 702/24 |
| 2008/0064975 | A1 * | 3/2008 | Hancock et al. | 600/532 |
| 2010/0002234 | A1 * | 1/2010 | Cormier et al. | 356/436 |
| 2010/0036274 | A1 * | 2/2010 | Assadi-Porter et al. | 600/532 |

OTHER PUBLICATIONS

Wahl E. et al. Applications of Cavity Ringdown Spectroscopy to High Precision Isotope Ratio Measurement of 13C/12C in Carbon Dioxide. Isotopes in Environmental and Health Studies 42(1)21-35, Mar. 2006.*
Bartlome R. et al. Laser Based Human Breath Analysis Optics Letters 34(7)1-13 Apr. 1, 2009.*
Modak A. Stable Isotope Breath Tests in Clinical Medicine: A Review. J Breath Research 1(1)Sep. 1-13, 2007.*
Butz, et al.; "Changes in the Natural Abundance of 13CO2/12CO2 in Breath Due to Lipopolysacchride-Induced Acute Phase Response"; Rapid Communications in Mass Spectrometry; 23; pp. 3729-3735; (2009).
Hellman, Bo; "Pulsatility of Insulin Release—a Clinically Important Phenomenon"; Upsala Journal of Medical Sciences; 114; pp. 193-205; (2009).
Hubbard, et al.; "Systems Analyses of Circadian Networks"; Molecular BioSystems; 5; pp. 1502-1511; (2009).
Lloyd, et al.; "Ultradian Metronome: Timekeeper for Orchestration of Cellular Coherence"; TRENDS in Biochemical Sciences; 30(7); pp. 373-377; (2005).
Novak et al.; "Design Principles of Biochemical Oscillators"; Nat Rev Mol Cell Biol; 9(12); pp. 981-991; (2008).
Smolensky et al.; "Role of Sleep-Wake Cycle on Blood Pressure Circadian Rhythms and Hypertension"; Sleep Medicine; 8; pp. 668-680; (2007).

* cited by examiner

*Primary Examiner* — Ralph Gitomer
(74) *Attorney, Agent, or Firm* — Cantor Colburn LLP

(57) ABSTRACT

The methods described herein are based on the observation that oscillations in breath isotope ratio data can be used for the purpose of identifying an "unhealthy" state in an organism such as a human. Described herein are methods of determining the state of health of an individual, such as the transition from healthy to infected, by identifying changes in oscillation modes in breath isotope ratio data. Changes in the frequency and/or amplitude of the oscillation modes are correlated with the heath of the individual. The methods can advantageously be used to provide information about the health of an individual in shorter periods of time than previous methods.

29 Claims, 6 Drawing Sheets

DETECTION OF RATE CHANGES IN SYSTEMATIC OSCILLATIONS OF METABOLIC ATHWAYS BY MONITORING ISOTOPE RATIOS

FEDERAL FUNDING STATEMENT

This invention was made with government support under LM008992 awarded by the National Institutes of Health. The government has certain rights in the invention.

FIELD OF THE DISCLOSURE

The present disclosure is related to the detection of the catabolic state in humans and organisms by detecting isotope ratios, e.g., carbon isotope ratios, in exhaled breath, specifically by determining the rate of systemic oscillations in the carbon isotope ratios.

BACKGROUND

Catabolism refers to the metabolic pathways that break down molecules such as polysaccharides, nucleic acids, lipids and proteins into smaller units, while anabolism refers to the metabolic pathways that construct molecules from smaller units. Catabolism produces energy, while anabolism requires energy. The catabolic state refers to the condition wherein the body uses stores of carbohydrates, amino acids, or fats as a source of energy for maintenance, thereby generating urinary nitrogen and $CO_2$ in breath. These changes will show up quickly in urine and breath. Body carbohydrates, amino acids, and fats are also a source of nutrients to synthesize defense products, e.g., immunoglobulins and acute phase proteins, which can be a function of the catabolic state. Hence, there can be concomitant anabolic processes occurring in an organism even during a general state of catabolism. The catabolic state may be induced by infection, disease, external pathogens, toxic chemical exposure, malnutrition, or other causes. Early detection of the onset of the catabolic state, as an indicator of a serious disease, has broad applications in human and veterinary health. In sepsis alone, the mortality rate of 44% (among 750,000 reported cases) can be cut in half through earlier detection and intervention.

A noninvasive, non-doping, rapid stable isotope method to discern the onset of the catabolic state by detecting isotopic changes in the exhaled $CO_2$ in breath was described in issued U.S. Pat. No. 5,912,178 (the '178 patent). The relative health of an organism was determined by comparing the sampled ratio ($C^{13}:C^{12}$) to a baseline ratio in the organism by testing breath samples in a mass spectrometer, for example. The methods disclosed in the '178 patent allow for a non-invasive determination of net catabolic processes of organisms experiencing altered organ function or a deficit in nutrient intake. One disadvantage to the method disclosed in the '178 patent is that a comparison specimen is required to determine if the organism from which a breath sample is measured is in a catabolic state.

Similarly, in U.S. Pat. No. 7,465,276 (the '276 patent), the relative amounts of first and second breath isotopes are measured over time to determine if an organism is experiencing a viral or bacterial infection. Advantages of the method of the '276 patent are that breath samples from an isotopically unenriched organism can be monitored for changes in isotope ratios over time to determine if the organism is experiencing a bacterial or viral infection. A disadvantage of the method is that a baseline measurement from the healthy subject is preferred so that changes from the baseline can be measured that are indicative of infection. In addition, it is generally advisable to obtain measurements over several hours or even several days so that the change in isotope ratio from the baseline ratio can be determined. Thus, determining the transition from a healthy to an infected organism within the short-term infection period, e.g., 30 minutes to 2 hours, may not be possible as the change in slope may not be measurable in this time period.

What is needed are additional methods to use the changes in isotope ratios in breath to determine the catabolic or infected state of an organism as well as the transition from healthy to sick to allow for prompt therapeutic intervention.

BRIEF SUMMARY

In one aspect, a method of determining if an individual is transitioning from a healthy state to an unhealthy state comprises:

monitoring breath taken from the individual and measuring a relative amount of a first isotope to a second isotope therein over a total time interval ($t_{total}$), wherein the individual is healthy during the time interval $t_{0\text{-}healthy}$, wherein $t_0$ is a time point at the start of time interval $t_{total}$, and $t_{healthy}$ is time point during $t_{total}$ in which the individual is healthy, identifying a healthy functional oscillation pattern in the relative amount of the first isotope to the second isotope therein during time interval $t_{0\text{-}healthy}$, identifying a test functional oscillation pattern in the relative amount of the first isotope to the second isotope therein a test time interval $t_{test}$ within $t_{total}$, wherein $t_{test}$ does not overlap $t_{0\text{-}healthy}$, and determining that the individual is transitioning from a healthy state to an unhealthy state when the healthy functional oscillation pattern and the test functional oscillation pattern are distinct in period of oscillation, oscillations per unit time, and/or variability in oscillation period, wherein the first and second isotopes are selected from the group consisting of a pair of $^{13}C$ and $^{12}C$, a pair of $^{15}N$ and $^{14}N$, a pair of $^{17}O$ and $^{16}O$, and a pair of sulphur isotopes.

In another aspect, a method of determining whether an individual is in an unhealthy state comprises:

monitoring breath taken from the individual and measuring a relative amount of a first isotope to a second isotope therein over a total time interval ($t_{total}$), wherein the individual is unhealthy during the time interval $t_{0\text{-}unhealthy}$, wherein $t_0$ is a time point at the start of time interval $t_{total}$, and $t_{unhealthy}$ is time point during $t_{total}$ in which the individual is unhealthy, identifying an unhealthy functional oscillation pattern in the relative amount of the first isotope to the second isotope therein during time interval $t_{0\text{-}unhealthy}$, identifying a test functional oscillation pattern in the relative amount of the first isotope to the second isotope therein a test time interval $t_{test}$ within $t_{total}$, wherein $t_{test}$ does not overlap $t_{0\text{-}unhealthy}$, and determining that the individual is transitioning from an unhealthy state to a healthy state when the unhealthy functional oscillation pattern and the test functional oscillation pattern are distinct in period of oscillation, oscillations per unit time, and/or variability in oscillation period, wherein the first and second isotopes are selected from the group consisting of a pair of $^{13}C$ and $^{12}C$, a pair of $^{15}N$ and $^{14}N$, a pair of $^{17}O$ and $^{16}O$, and a pair of sulphur isotopes.

In yet another aspect, a method of determining the severity of an infection in an individual comprises:

monitoring breath taken from the individual and measuring a relative amount of a first isotope to a second isotope therein over a time period (t), wherein the first and second isotopes are selected from the group consisting of a pair of $^{13}$C and $^{12}$C, a pair of $^{15}$N and $^{14}$N, a pair of $^{17}$O and $^{16}$O, and a pair of sulphur isotopes;

identifying for the individual a functional oscillation pattern in the relative amount of the first isotope to the second isotope therein over the time period (t), and determining any differences between the functional oscillation pattern for the individual compared to an average functional oscillation pattern for a healthy and/or infected reference population, wherein the degree of difference between the functional oscillation pattern for the individual and the average functional oscillation pattern for the reference populations determines the severity of the infection.

In a still further aspect, a method of determining whether an individual is in an unhealthy state comprises:

monitoring breath taken from the individual and measuring a relative amount of a first isotope to a second isotope therein over a time period ($t_{total}$) wherein the first and second isotopes are selected from the group consisting of a pair of $^{13}$C and $^{12}$C, a pair of $^{15}$N and $^{14}$N, a pair of $^{17}$O and $^{16}$O, and a pair of sulphur isotopes, identifying a functional oscillation pattern in the relative amount of the first isotope to the second isotope therein over the time period ($t_{total}$), and comparing the functional oscillation pattern for the individual with a functional oscillation pattern averaged across a known healthy and/or unhealthy reference population, and determining that the individual is in an unhealthy state when the functional oscillation pattern for the individual is different in frequency and/or amplitude to the averaged functional oscillation pattern for the healthy and/or infected reference population.

BRIEF DESCRIPTION OF THE DRAWINGS

FIG. 8 shows three examples of randomly selected 30-minute data regions (boxes) used to establish a comparison database for testing if a breath carbon delta value oscillation pattern of an animal with an unknown health condition. Breath carbon delta oscillation data from known healthy and lipopolysaccharide-stimulated animals was used to create a database of oscillation pattern that represent both healthy and disease states. Data was also collected from animals fed different diets since it is known that diet can affect the delta value (raw data not shown, but similar to FIG. 8). Data within a health status and or diet were combined for use in comparison to a data set from an unknown condition. (see example for description of data management).

Figure 1:
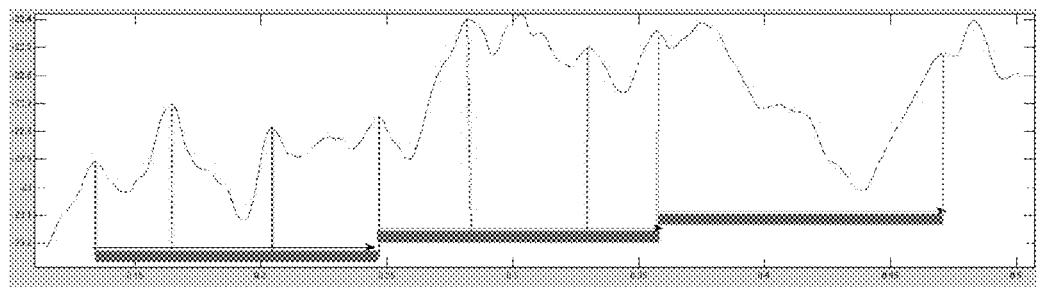
FIG. 1 shows evidence of oscillations in breath delta values in data collected from a human subject. Raw breath delta values were collected every second for 30 minutes from a healthy human subject using an isotopic analyzer. Raw data was smoothed using a standard Savitzky-Golay filter (order=2). The sum of modes 3 and 4 generated by a Hilbert-Huang transformation of smoothed oscillation data is shown. The X-axis represents 30 minutes of sampling (0.5 hr). The Y-axis is the actual breath carbon delta value. Within the three fixed time intervals (shown by bold horizontal bar), repeating oscillations with variable frequencies are observed. Interval 3 shows a "missing" oscillation peak. Vertical lines illustrate both the repetitive and complex nature of the oscillation pattern that can make simple quantitative analysis challenging, but mathematically feasible.

The above-described and other features will be appreciated and understood by those skilled in the art from the following detailed description, drawings, and appended claims.

DETAILED DESCRIPTION

The present disclosure is directed to the use of newly discovered oscillations in exhaled breath isotope ratio data for the purpose of identifying an "unhealthy" state in an organism such as a human. Oscillation patterns have been identified in human breath data as well as in a mouse endotoxemia model of a healthy and unhealthy state. Oscillations in healthy and unhealthy subjects can be distinguished using standard analytical methods. In addition, machine learning tools known in the art can be applied to oscillation data and used to classify oscillation differences between healthy and unhealthy subjects irrespective of the diet of the subject. As used herein, the terms unhealthy, sick, and infected all refer to a state that is the absence of "health," which is reflected in changes in the oscillation patterns of isotope ratios in exhaled breath. The methods disclosed herein can be used in clinics as a point of care (POC) test to determine the status of a patient and their type of infection. In addition, the methods can be used in veterinary clinics for similar tests on animals. While the methods described are useful in organisms enriched with a stable isotope, advantageously the methods can also be performed on isotopically unenriched individuals.

As used herein, the term individual refers to humans and animals, including all vertebrate animals, particularly mammals such as dogs, cats and horses, and birds such as chickens and turkeys.

In one embodiment, the methods disclosed herein are used to detect an unhealthy state, such as a disease state or an infected state of an individual. Fighting infections, for example those that are bacterial in origin, requires rapid protein breakdown to supply the high energy and raw material requirements (e.g., amino acids) for antibody production and other anti-infection responses. Certain isotopic ratios of proteins, fats, and carbohydrates stored in body tissues differ from the isotopic ratio of metabolized food, and when a catabolic state is induced by infection the body begins to consume stored tissue, which (due to the different ratios in the stored tissue) results in a change in the ratios in breath (e.g., exhaled $^{13}CO_2$ content). Similarly, different disease states cause changes in protein substrates and metabolism. In addition, the "kinetic isotope effect", where molecules participate in different chemical reactions based on their isotopic weight, can also be influenced by disease or infection. As shown herein, in addition to a change in the slope of the isotope ratios, there is also a change in the inherent oscillation pattern in the isotope ratios which can be detected on a shorter time scale than the slope. Advantageously, different diseases and infection, for example, will modify isotope oscillation patterns in different ways, thus allowing for a general diagnostic mechanism based on changes in isotope oscillation patterns.

The heavy isotope to light isotope ratios measured in breath become more negative in the presence of infection or an acute phase response to a disease state. This means that the relative amount of light isotope in breath is increased and the amount of heavy isotope is decreased. The reason for this shift in the relative abundance of heavy isotope is due to the kinetic isotope effect. Molecules such as amino acids can be used either for fuel or protein synthesis. During infection or in an acute disease state, the molecules most likely to be used for fuel and thus converted to $CO_2$ are molecules that do not contain $^{13}C$, hence breath becomes enriched with $^{12}C$ during infection or during an acute disease state. Molecules that contain $^{13}C$ stay with the body and are used for the synthesis of new proteins, such as antibodies and other proteins required during the acute disease state. The change is believed to be a direct reflection of the increasing use of body tissue for "fuel" ($^{12}C$ molecules) versus protein synthesis ($^{13}C$ molecules). Absent of an infection or the induction of an acute disease state response, breath $CO_2$ resembles the isotope ratios found in the body.

During bacterial infection, for example, immune responses (acute and involving the innate immune system) to the invasion are marked by a sudden release of catabolic cytokines within the first hour of infection. These cytokines consist of tumor necrosis factor (TNF), and interleukins (IL) 1 and 6. These three cytokines result in the rapid redistribution of body nutrients, such as amino acids. For example, TNF and IL-1 will induce the degradation of skeletal muscle resulting in a release of amino acids that can be used to make immune and inflammatory acute phase proteins or used as an energy source. The fractionation of the carbon isotopes occurs as amino acids flow toward either toward protein synthesis versus burned as fuel.

While viral infections can also induce carbon fractionation and more negative breath carbon delta values, when contrasted to bacterial infection initiation, the cytokines associated with early stages of viral infections cause the release of different cytokines, namely the interferons. Carbon fractionation associated with viral infections can yield different patterns, such as patterns linked to the reproductive stage of the virus.

It was previously shown that there is a distinct change in isotope ratio amounts within about 2 hours after bacterial challenge begins, followed by relatively stable, albeit changed from the unchallenged individuals, ratios for a prolonged period. In contrast, a virally challenged host exhibits a series of periodic modifications, beginning significantly later (e.g., 2-3 days). Also, in the case of bacterial infection, the breath becomes "lighter" at a greater rate of speed than during a viral infection. Hence, the speed of change, as well as the presence or absence of the repeated spikes in the ratio pattern indicative of a viral life cycle, are indications of the type of infecting agent.

Similar to what is observed in infection, trauma, burns and surgery can also affect the disease/health state of a subject, particularly the acute phase of disease, and can result in distinct changes in the isotope ratio amounts. The changes in the isotope ratio amounts and also the oscillations should be more pronounced during the acute disease phase because the changes in protein metabolism are greater during the acute disease phase.

Thus, changes in the isotope ratios in breath over time can be used to determine the healthy/unhealthy state of an individual. However, for humans, it is possible to obtain a baseline reading for a patient at an annual physical or at another opportunity when the patient is otherwise at a medical facility and not complaining of symptoms of illness. Alternatively, the first reading could be when a patient first complains of infection or disease type symptoms (e.g., particularly elevated temperature). In another aspect, the data for an individual can be compared to the averaged data for a population of individuals of the same species.

It has been unexpectedly found by the present inventors that breath isotope ratios have oscillation modes in healthy as well as unhealthy individuals, and that the oscillation modes are different in healthy and sick individuals. These oscillations are superimposed on the downward slope in isotope ratios over time. Thus, by measuring the oscillations in isotope ratios in breath, one can obtain, independent of the slope of the change in ratio, an indication of the catabolic state/ health of an individual. The measurement of the oscillation frequency of the isotope ratios is distinct from absolute monitoring of the breath isotope ratios. Measuring changes in oscillation frequency of isotope ratios can advantageously be used to determine if an individual is transitioning from a healthy state to an unhealthy state, to determine whether an individual is in an unhealthy state, and to determine if an individual is transitioning from an unhealthy state to a healthy state. Advantageously, the unhealthy state of the individual can be determined without knowledge of the isotope ratio frequency patterns of the individual in the healthy state. An advantage of the use of oscillation modes is that the state of the organism can be determined in a shorter period of time than that required to determine a slope, e.g., 35 minutes compared to 2 hours. Another advantage of the use of oscillation modes is that the diet consumed by the organism does not interfere with the ability to detect health status and if the health status is fixed, clues about diet status can be discerned.

In the methods disclosed herein, breath taken from the individual over time is used to measure the relative amount of a first isotope to a second isotope therein over time, wherein the first and second isotopes are, for example, the pair of $^{13}C$ and $^{12}C$, but might also be alternatively the pair of $^{15}N$ and $^{14}N$, or the pair of $^{17}O$ and $^{16}O$, or a pair of sulphur isotopes (e.g., $^{32}S$ and $^{34}S$; $^{33}S$ and $^{36}S$).

In one embodiment, relative isotope measurements are made using cavity ringdown spectroscopy. In a specific embodiment, measurements are made using a spectrometer with frequent sample collection, e.g., every second, so that the oscillation modes can be determined. An exemplary instrument is a Picarro G2101-i Isotopic $CO_2$ analyzer. In one embodiment, measuring a relative amount of the first isotope to the second isotope therein over a total time interval ($t_{total}$) includes continuous measurement or measurement over discrete time points ($t_p$) and discrete time intervals ($t_i$) within the time period ($t_{total}$). Discrete time intervals could be during a healthy state ($t_{healthy}$), unhealthy state ($t_{unhealthy}$), or during an unknown or testable state ($t_{test}$). In one embodiment, the time point ($t_p$) between measurements is one second and discrete time interval ($t_i$) is one minute to one hour.

In one embodiment, a method of determining if an individual is transitioning from a healthy state to an unhealthy state comprises monitoring breath taken from the individual and measuring a relative amount of a first isotope to a second isotope therein over a total time interval $t_{total}$, wherein the individual is healthy during the time interval $t_{0\text{-}healthy}$, wherein $t_0$ is a time point at the start of time interval $t_{total}$, and $t_{healthy}$ is time point during $t_{total}$ in which the individual is healthy, identifying a healthy functional oscillation pattern in the relative amount of the first isotope to the second isotope therein during time interval $t_{0\text{-}healthy}$, identifying a test functional oscillation pattern in the relative amount of the first isotope to the second isotope therein a test time interval $t_{test}$ within $t_{total}$, wherein $t_{test}$ does not overlap $t_{0\text{-}healthy}$, and determining that the individual is transitioning from a healthy state to an unhealthy state when the healthy functional oscillation pattern and the test functional oscillation pattern are distinct in period of oscillation, oscillations per unit time, and/or variability in oscillation period, wherein the first and second isotopes are selected from the group consisting of a pair of $^{13}C$ and $^{12}C$, a pair of $^{15}N$ and $^{14}N$, a pair of $^{17}O$ and $^{16}O$, and a pair of sulphur isotopes, and wherein measuring is continuous measurement or measurement at discrete time points within time period $t_{total}$.

In another embodiment, a method of determining if an individual is transitioning from an unhealthy state to a healthy state comprises monitoring breath taken from the individual and measuring a relative amount of a first isotope to a second isotope therein over a total time interval $t_{total}$, wherein the individual is unhealthy during the time interval $t_{0\text{-}unhealthy}$, wherein $t_0$ is a time point at the start of time interval $t_{total}$, and $t_{unhealthy}$ is time point during $t_{total}$ which the individual is unhealthy, identifying an unhealthy functional oscillation pattern in the relative amount of the first isotope to the second isotope therein during time interval $t_{0\text{-}unhealthy}$, identifying a test functional oscillation pattern in the relative amount of the first isotope to the second isotope therein a test time interval $t_{test}$ within $t_{total}$, wherein $t_{test}$ does not overlap $t_{0\text{-}unhealthy}$, and determining that the individual is transitioning from an unhealthy state to a healthy state when the unhealthy oscillation pattern and the test oscillation pattern are distinct in period of oscillation, oscillations per unit time, and/or variability in oscillation period, wherein the first and second isotopes are selected from the group consisting of a pair of $^{13}C$ and $^{12}C$, a pair of $^{15}N$ and $^{14}N$, a pair of $^{17}O$ and $^{16}O$, and a pair of sulphur isotopes, and wherein measuring is continuous measurement or measurement at discrete time points within time period $t_{total}$.

In one embodiment, the method of determining if an individual is transitioning from an unhealthy state to a healthy state, or a healthy state to an unhealthy state further comprises determining a slope by determining the change in the relative amount of the first isotope to the second isotope changes from time $t_x$ to time $t_y$ within time period $t_{total}$.

While oscillations in the relative amount of a first to a second isotope in breath are readily observable by visual inspection, the oscillatory patterns are complex. Certain modes, for example, can be readily identified by their frequency as "instrument noise"—this is the result of uncertainties in the rapid continuous measurement. Standard mathematical tools to smooth (Savitzky-Golay filter, order=2) and analyze data such as a Hilbert-Huang transformation and Fourier analysis can be used to decouple the different functional oscillation patterns and define the nature of the oscillation frequencies.

Whatever the method used to decompose/transform the data, the functional oscillation patterns used to define the healthy animal will be distinct from the unhealthy animal Reliable data for the separation of the oscillatory patterns of isotope ratios, using raw data smoothed with second order Savitzky-Golay, transformed with Hilbert-Huang analytical methods, and analyzed with Fourier analysis shows that healthy patients have, a functional oscillation pattern (e.g., a dominant oscillation)—an oscillation pattern that is observed to persist throughout the measurement time and across measurements of different healthy animals. The appearance of a healthy functional oscillation pattern is the criteria to define the health status of the individual. The evidence of a healthy functional oscillation pattern of isotope ratios in breath using this type of analysis defines the healthy individual, and a change (e.g., loss of a dominant frequency) in the healthy functional oscillation pattern resulting in an unhealthy functional oscillation pattern in the individual is indicative of a transition from healthy to unhealthy. Further, the healthy functional oscillation pattern is restored when the individual transitions back from sick to healthy. Qualitatively, a functional oscillation pattern resulting from smooth raw data transformed by Hilbert-Huang and analyzed by Fourier, in the healthy individual, results in a single dominant frequency of oscillations in a specified frequency range, while in the unhealthy individual frequency domination is lost, multi-frequencies become evident and a shift in the oscillation frequency is observed.

As used herein, a "functional oscillation pattern" is a decomposed/transformed oscillation derived from smoothed raw data in a relative amount of first isotope to second isotope in a time period such that the analysis yields a functional oscillatory pattern that contains at least 3 oscillatory cycles per measurement period, but preferably 4 or more oscillatory cycles per measurement period. In one embodiment, within this analysis, the healthy individual has a typical average period of oscillation of 6 to 7 minutes or an oscillation frequency of 8.5 to 10 cycles per hour. The typical average period of oscillation in the unhealthy individual is increased to 8 to 9 minutes or an oscillatory frequency of 6.5 to 7.5 cycles per hour; this reflects a change of at least 10% in the typical period of oscillation. In addition, in the typical case for an unhealthy individual, instability in the period of oscillation, in the form of additional oscillation modes with frequencies different from the healthy state (for example, 10% change), is found to be present relative to the healthy individual. The reason for the increased mean period of oscillation as well as the increased variability in oscillation period is due to a disruption in the oscillatory pattern of the unhealthy individual. Depending on the method of analysis, the healthy individual can be distinguished from the unhealthy individual based on the oscillation pattern (via pattern recognition), the average period of oscillations, the oscillations cycles per hour, or the degree of variability in oscillation period. As used herein, the period of oscillation is the time of one cycle of the repeating pattern that defines the functional mode, or the peak-to-peak time in the functional mode. The oscillation frequency is the number of oscillations per unit of time (e.g., one hour). It should be noted that the raw data in a relative amount of first isotope to second isotope in a time period may have multiple functional oscillation patterns that differ in both period of oscillation and oscillation frequency, and that a first, second, third etc. functional oscillation pattern may change upon a change in the catabolic state/health of the individual. In addition to one or more dominant oscillation frequencies, the data may have one or more minor oscillation frequencies that may be useful in distinguishing the health of the individual.

In sum, the functional oscillation pattern is the pattern that defines the healthy individual or the time $t_{ihealthy}$ value from which measurements are taken. Time $t_{unhealthy}$ represents the time at which the individual is different from $t_{healthy}$, that is, the time in which there is a change in the catabolic state/health of the individual. Further, when the individual changes from an infected or catabolic state to a healthy state, it is expected that the modified functional oscillatory pattern will substantially revert back to the first functional oscillatory pattern.

In one embodiment, the first functional oscillatory pattern in the relative amount of the first isotope to the second isotope is a low frequency oscillation having an oscillation period of 6 to 12 minutes.

In the method of determining if an individual is transitioning from a healthy to an unhealthy state, two changes in the relative amounts of the first and second isotopes may be measured. First, the functional oscillatory pattern in the relative amount of the first isotope to the second isotope changes in frequency and/or amplitude between time t, and time $t_x$. In addition, the relative amount of the first isotope to the second isotope changes from the relative amount at $t_0$ to a relative amount at time $t_x$ within the time period (t). This is the decrease in slope upon transitioning to an unhealthy state that had been previously identified. Thus, a change in slope and/or a change in a functional oscillatory pattern determines a change from healthy to unhealthy. As used herein, changes in oscillation frequency and/or oscillation period between time t, and time $t_{ix}$ means that functional oscillatory pattern changes in oscillation period and/or splits to produce more frequencies that were not present at time $t_i$. In one embodiment, the change in frequency and/or dominance of frequency in the functional oscillatory pattern in the individual in the unhealthy state results in an irregular oscillation pattern that contains multiple dominant frequencies. Such changes can be detected by subjecting the data to mathematical tools known in the art.

One advantage of the methods disclosed herein is that breath isotope data can be taken for shorter periods of time than in the prior methods where only the slope of the changes was measured. In one embodiment, the time period t is less than 2 hours, less than 90 minutes, less than 1 hour, less than 45 minutes, less than 35 minutes, less than 20 minutes, less than 10 minutes, to as little as 5 minutes. Data collection need be done only over a time period that is sufficient to establish the oscillation pattern. While 30 minutes is generally a suitable time period for data collection in humans and mice under normal conditions, the time period can be shortened depending on the stage of infection, the sensitivity and precision of the instrument, the level of established prior data to be used as comparative template, and other factors (e.g., early infection may require a longer sampling period).

In one embodiment, the method further comprises identifying a second functional oscillatory pattern in the relative amount of the first isotope to the second isotope therein over the time period ($t_{total}$), wherein the second functional oscillatory pattern in the relative amount of the first isotope to the second isotope changes in frequency and/or dominance between time $t_i$ and a time $t_{ix}$ within the time period (t).

In a specific embodiment, identifying the functional oscillatory pattern in the relative amount of the first isotope to the second isotope therein over a time period (t) comprises decomposing the relative amount of the first isotope to the second isotope therein over the time period (t) to produce a finite number of embedded oscillatory patterns wherein an analysis of the embedded oscillatory pattern can be conducted. This process can be conducted by sequentially extracting oscillatory frequencies, beginning with the lowest frequency from raw data until the embedded frequency has 4 to 15 oscillatory periods (cycles) per hour. When data is transformed using Hilbert-Haung methods, said embedded frequency is defined as an intrinsic mode. A functional oscillatory pattern can be calculated from an intrinsic mode using Fourier analysis. The method optionally further includes identifying high frequency oscillation modes (e.g., greater than 15 cycles per hour) using mode decomposition, and filtering (Golay Filter) the high frequency oscillation modes from the relative amount of the first isotope to the second isotope therein over the time period (t).

As used herein, a modified functional oscillatory pattern is defined as an oscillation pattern in a time interval that is modified or changed from the healthy or unhealthy functional oscillatory pattern and indicates a change in the health status of the individual. By modified, it means that the healthy functional oscillatory pattern changes in its frequency and/or oscillation period, that is, the healthy functional oscillatory pattern shifts to lower frequencies or evidence of a single dominant frequency changes to multiple frequencies with two or more oscillation periods that were not present in the oscillation patterns when the individual was healthy. In one embodiment, the modified functional oscillatory pattern is an irregular oscillation pattern that contains multiple oscillation frequencies.

In one embodiment, the healthy/unhealthy functional oscillatory pattern and the modified functional oscillatory pattern are independent of the diet of the individual. While the relative ratio of isotopes and the baseline measurement may be affected by the diet of the individual, the functional oscillation patterns are independent of diet. This is a distinct advantage over the prior methods where diet could potentially influence the data interpretation.

In one embodiment, the oscillation period of the healthy functional oscillatory pattern changes by more than 10% when the individual transitions from a healthy state to an unhealthy state. In a specific embodiment, the oscillation period of the healthy functional oscillatory pattern changes by 10% to 30% when the individual transitions from a healthy state to an unhealthy state. Similarly, the oscillation period of the unhealthy functional oscillatory pattern changes by more than 10% when the individual transitions from an unhealthy state to a healthy state. In a specific embodiment, the oscillation period of the unhealthy functional oscillatory pattern changes by 10% to 30% when the individual transitions from an unhealthy state to a healthy state A distinct advantage of the methods disclosed herein is that they can be performed in a continuous manner in a hospitalized patient such as an intubated patient. This is particularly advantageous in the early detection of sepsis.

For confined non-human organisms, or populations of such organisms, regular monitoring could be conducted on a continuous basis. Alternatively, similar principles could be applied with respect to monitoring the health of humans in an apartment building on an overall basis.

In another embodiment, a method of determining whether an individual is in an unhealthy state, the method comprises monitoring breath taken from the individual and measuring a relative amount of a first isotope to a second isotope therein over a time period ($t_{total}$), wherein the first and second isotopes are selected from the group consisting of a pair of $^{13}C$ and $^{12}C$, a pair of $^{15}N$ and $^{14}N$, a pair of $^{17}O$ and $^{16}O$, and a pair of sulphur isotopes, identifying a functional oscillation pattern in the relative amount of the first isotope to the second isotope therein over the time period ($t_{total}$), and comparing the functional oscillation pattern for the individual with a functional oscillation pattern averaged across a known healthy and/or unhealthy reference population, and determining that the individual is in an unhealthy state when the functional oscillation pattern for the individual changes is different in frequency and/or amplitude to the averaged functional oscillation pattern for the healthy and/or infected reference population.

Ideally the reference populations should be composed of at least 6 individuals within each population (healthy n>5 individuals, and unhealthy n>5 individuals). Data used for comparison of the test individual to the reference population could include raw data and/or smoothed and decomposed data. Many tools can be used to compare test data to reference populations including analytical methods or pattern recognition algorithms.

In a further embodiment, a method of determining the severity of an infection in an individual comprises monitoring breath taken from the individual and measuring a relative amount of a first isotope to a second isotope therein over a time period (t), wherein the first and second isotopes are selected from the group consisting of a pair of $^{13}C$ and $^{12}C$, a pair of $^{15}N$ and $^{14}N$, a pair of $^{17}O$ and $^{16}O$, and a pair of sulphur isotopes;

identifying a functional oscillation pattern in the relative amount of the first isotope to the second isotope therein over the time period (t), and determining any differences between the functional oscillation pattern for the individual compared to an average functional oscillation pattern for a healthy and/or infected reference population, wherein the degree of difference between the functional oscillation pattern for the individual and the average functional oscillation pattern for the reference populations determines the severity of the infection.

"Degree of difference" depends on method of pattern comparison. If computational analysis permits quantitative assessment, degree of difference is defined statistically based on the p value (probability), wherein the lower the probability of being the same, the greater the severity of infection. Where "degree of difference" cannot be computed in a quantitative manner, then severity is a function of the range of responses used to define the average populations. The closer the individual fit the range of the oscillatory pattern of the known infected population of like severity, the more the individual matches that degree of severity.

Two nonlimiting methods for distinguishing healthy and unhealthy are exemplified herein. Other methods can be constructed along similar lines using algorithms known in the art using the general framework described herein. Depending upon the application, monitoring may be performed essentially continuously pre- and post-infection (e.g., in a hospital/surgical setting), monitoring may be performed only post-event (e.g., in broader clinical settings where comparison to a reference population is possible, and where pre-event data that was collected previously (e.g., a month prior) for the patient (e.g., a weight loss patient) is available in addition to the post-event data. These applications are distinguished primarily by the output they generate rather than by the method of processing the input. In the case where continuous monitoring (pre/post method) can be performed, a continuous trace can be generated and compared against a "threshold" where crossing indicates a "state change"—for example, from healthy to sick. That is, when a continuous stream of data is available, e.g., for longer than about 35 minutes, a continuous stream of output or numerical indices (e.g., probabilities) can be produced. In the clinical setting, in contrast, the output can be a binary value (e.g., sick vs. healthy) with an associated confidence value. That is, the output can be a single index rather than multiple values. Population values, as well as the patients' own range of changes, define a "band" of healthy vs unhealthy state. At any point of time, the current mode of oscillation resides some place in the "band of values". The degree with which these values lie close to the "healthy edge" of this band or the "unhealthy edge" of this band defines the probabilities of transition to health or sickness.

Figure 2:
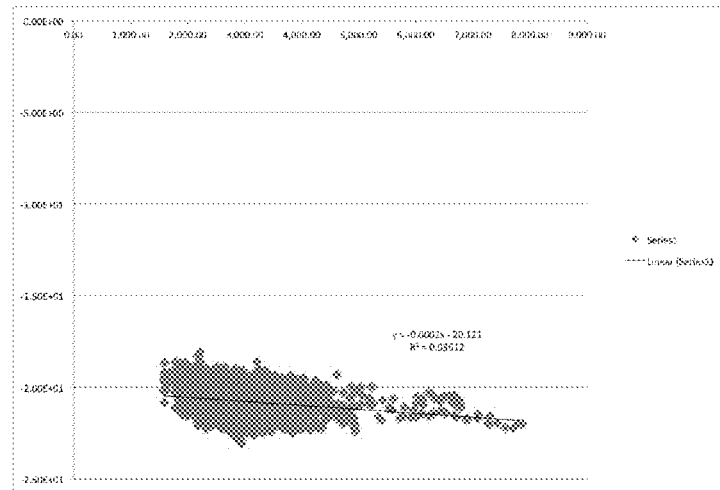
FIG. 2 shows the correlation between variations in breath $CO_2$ (Y-axis) versus change in breath carbon delta value (X-axis). The low $R^2$ shows that changes in breath carbon delta values are independent of changes in breath $CO_2$ concentrations.
Figure 3:
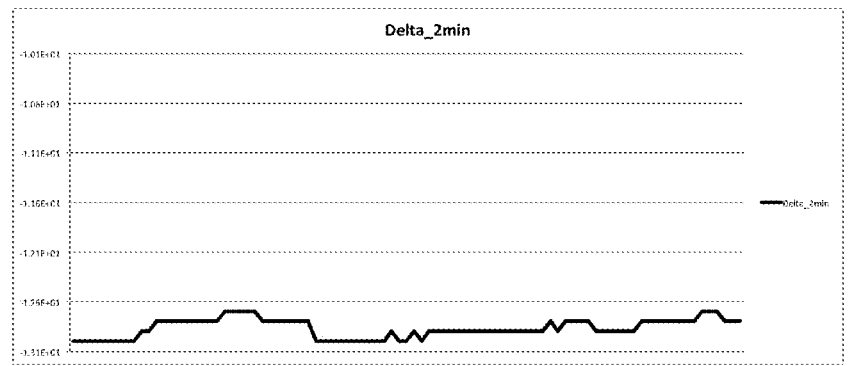
FIG. 3 shows the carbon delta value of room air measured every second using an isotopic analyzer. The total time in the X-axis is 60 minutes with a 2 minute interval shown by the bar length. The carbon delta value of room air was approximately −13 and the carbon delta value of room air measured over time was absent of oscillatory patterns.
Figure 4:
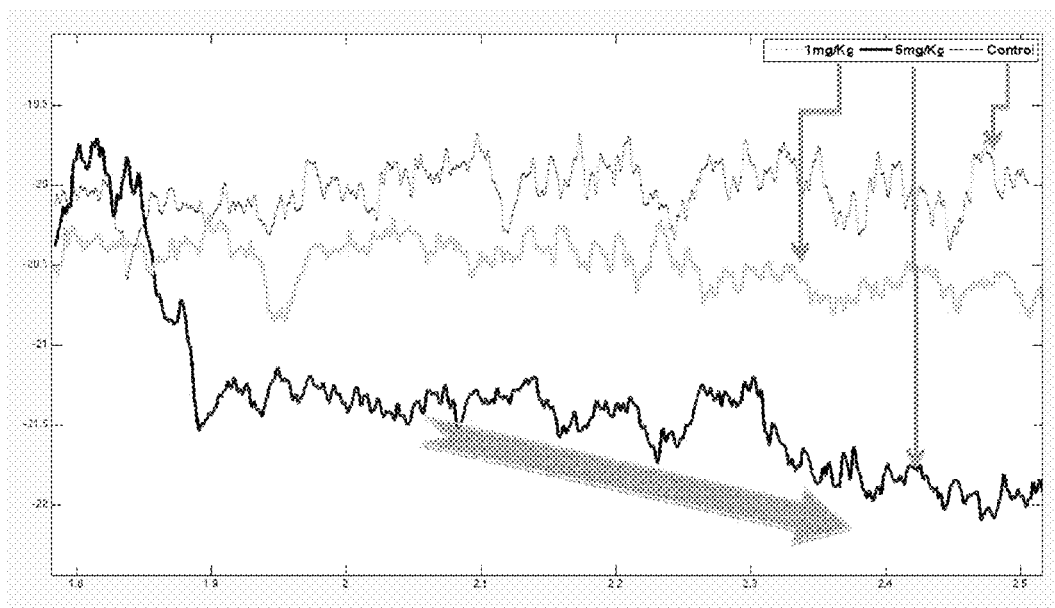
FIG. 4 shows the raw carbon delta value of individual mice (n=3/treatment) measured every second using an isotopic analyzer. One mouse from each treated group is selected for display in order to reduce the density of data. The X-axis is hours post injection and the Y-axis is breath carbon delta value. Values of mice in "dotted-thin" line were injected ip with sterile saline, "light-thick" with 1 mg lipopolysaccharide (LPS)/Kg body weight, and "dark-thick" 5 mg lipopolysaccharide/Kg body weight. Arrows from the legend box identify corresponding traces. The declining trend line (large arrow) of the breath carbon delta value is clearly present amidst oscillatory patterns for animals injected with 5 mg/kg LPS.
Figure 5:
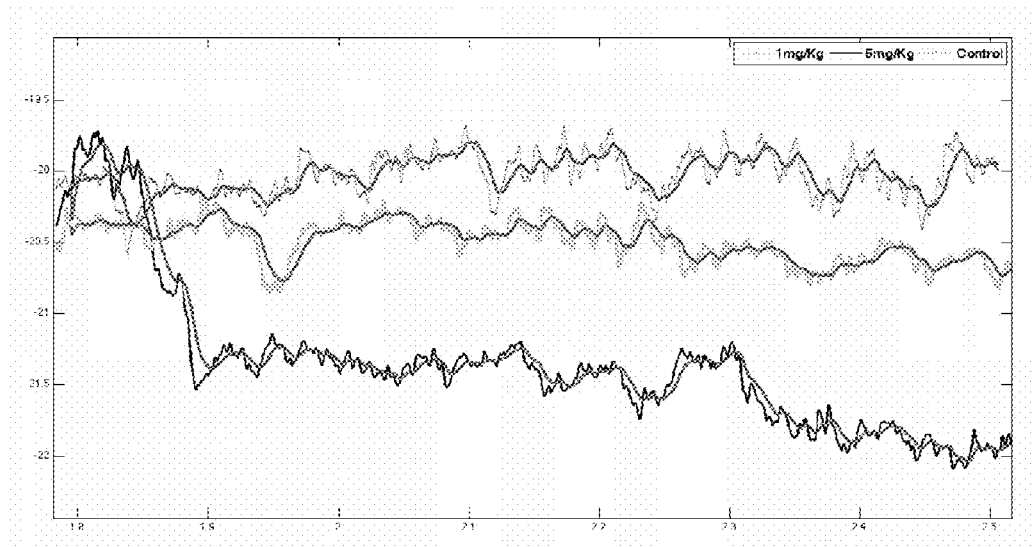
FIG. 5 illustrates the impact of data smoothing on the raw data shown in FIG. 4. Data is normalized and smoothed using a standard Savitzky-Golay filter (order=2) to further reveal the presence of a complex pattern in breath carbon delta value oscillations.
Figure 6:
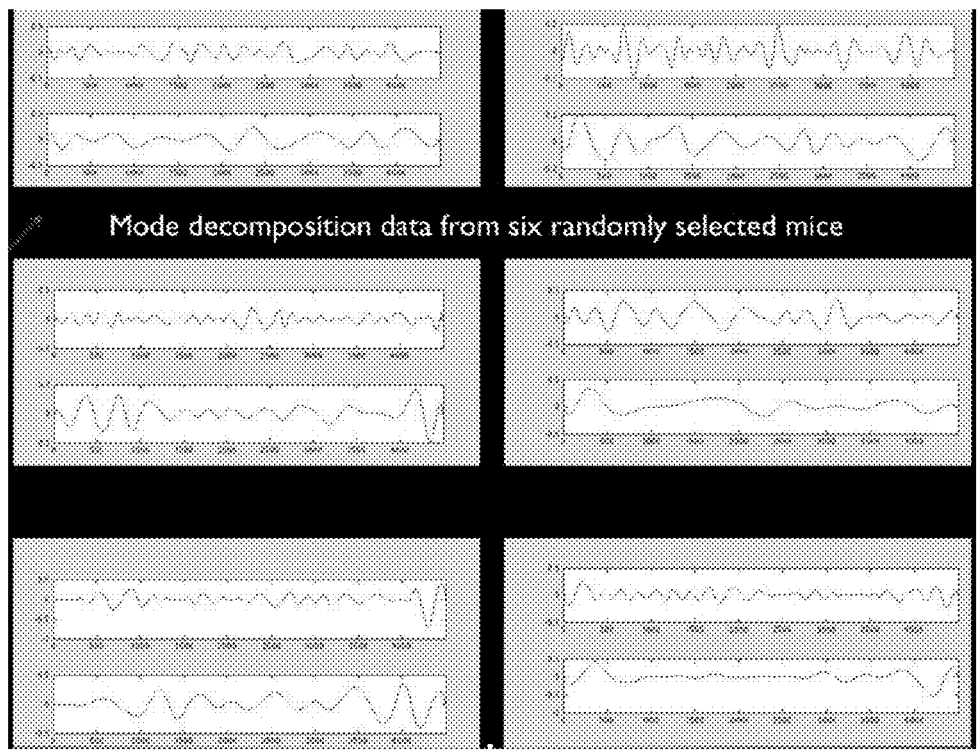
FIG. 6 shows two modes of Hilbert-Huang transformed breath carbon isotope delta values. Raw breath carbon delta values (such as shown in FIG. 4) from 6 healthy animals over a 4500 second collection period was smoothed using a standard Savitzky-Golay filter (order=2) (to create data such as shown in FIG. 5) then decomposed using a Hilbert-Huang transformation in order to clearly reveal the oscillatory patterns. Within each block shown (block=mouse) data was Hilbert-Huang (HH) transformed into 7 modes where with each successive mode transformation, the lowest oscillation frequencies were extracted. Hilbert-Huang transformed modes that had higher frequencies and had 4 to 15 oscillations per hour were selected for further Fourier analysis. Two Hilbert-Huang transformed are shown for each mouse (typically HH modes 3 and 4). X-axis is in seconds, Y-axis is oscillation scale according to HH decomposition (a scale free measure).
Figure 7:
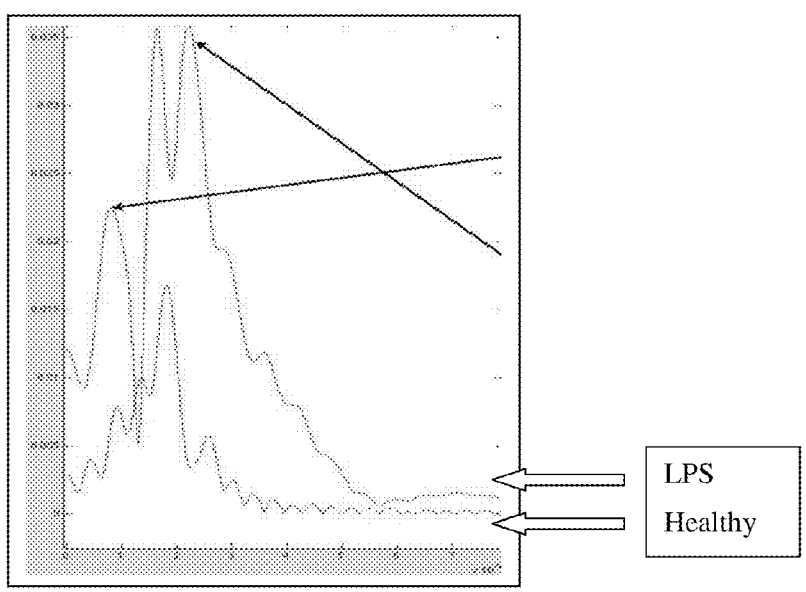
FIG. 7 is a Fourier analysis of a "30 minute" segment of the selected frequency mode (shown in FIG. 6 and described in legend for FIG. 6) generated by a Hilbert-Huang (HH) transformation (of normalized oscillation data) for healthy and lipopolysaccharide (LPS)-injected mouse. In the Fourier analysis of HH transformed data, healthy animals showed a dominant frequency with numerous less dominate frequencies. In the case of animals injected with LPS, the identity of the healthy functional oscillation pattern is lost and one or more modified functional oscillation patterns become evident. Y- and X-axes are arbitrary units.
Figure 8:
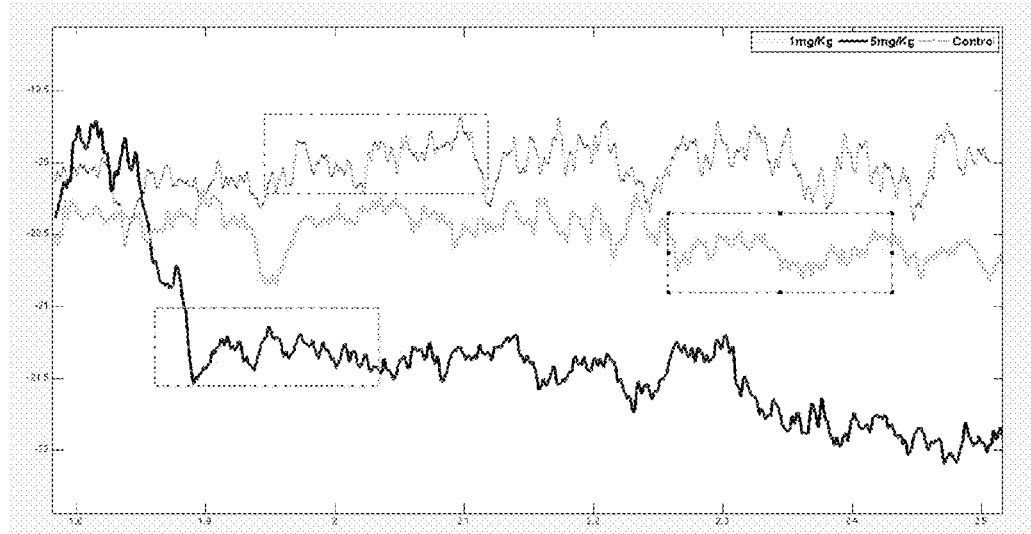
FIG. 8 shows three examples of randomly selected data regions (boxes) used to establish a comparison database for testing if a breath carbon delta value oscillation pattern of an animal with an unknown health condition. Boxes are drawn at half-scale to reduce clutter and illustrate the concept—they are not drawn to scale. Boxes selected during data analysis capture a 30-minute segment of breath carbon delta values. Breath carbon delta oscillation data from known healthy and lipopolysaccharide-stimulated animals was used to create a database of oscillation pattern that represent both healthy and disease states. Data was also collected from animals fed different diets since it is known that diet can affect the delta value (raw data not shown, but similar to FIG. 8). Data within a health status and or diet were combined for use in comparison to a data set from an unknown condition. (see example for description of data management).
Figure 9:
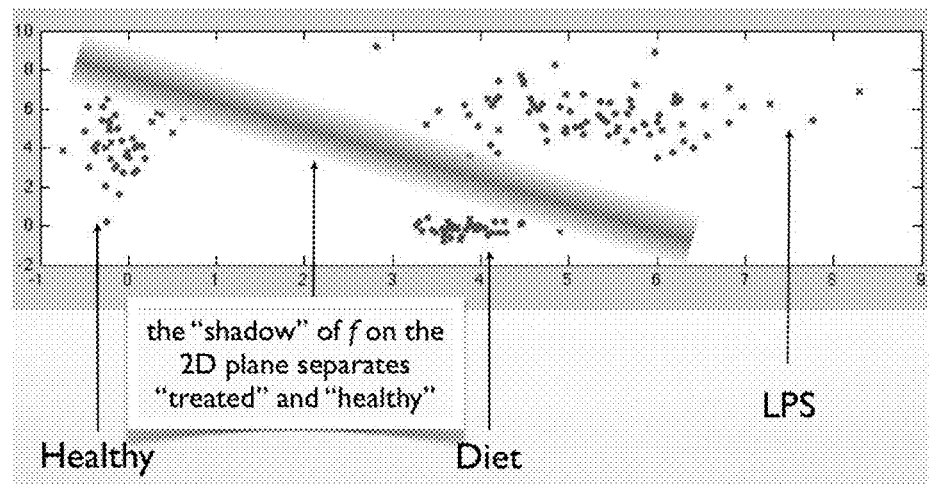
FIG. 9 shows a lower dimensional projection of the time series collected from each reference data box shown in FIG. 8. Estimator $f$ (see example for calculation) calculates times series data to the $70^{th}$ dimension. In this figure, $f$ for each time series is shown as a single point on a 2D plane. Healthy and lipopolysaccharide (LPS) injected animals points cluster separately along the arbitrary X- and Y-axis. A change in diet within a healthy population of animals also clusters. The "shadow" bar demonstrates that the clustering of $f$ values for each time sequence provides complete separation of healthy versus "unhealthy" (LPS-injected) animals. Diet also influences the $f$ value, however diet does not interfere with the ability to separate healthy versus unhealthy animal based on breath carbon delta value oscillation patterns as defined by f.
Figure 10:
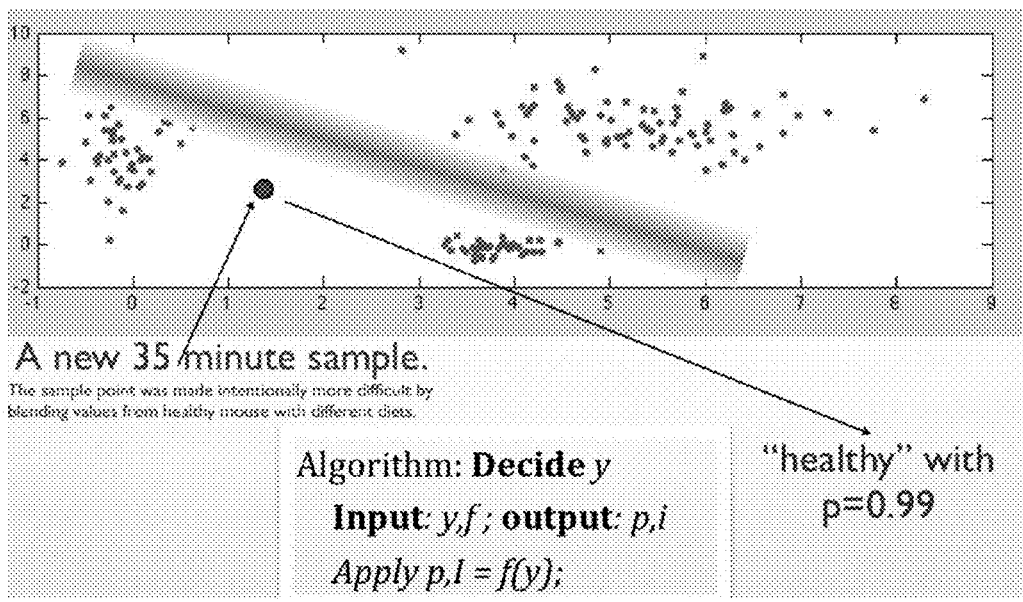
FIG. 10 represents a 2-D image of the described algorithm (see example for explanation) for detecting if a 35 minute time series breath carbon delta values of a known health status, but created by blending data from animals from two diets, could adequately measure health status. With 99% confidence, the healthy breath sample was distinguishable from the breath sample database of unhealthy animals. This experiment also demonstrates that diet is not a confounding factor in distinguishing healthy versus unhealthy status when based on breath oscillations of carbon delta values. The experiment shown also demonstrates that the described method of comparing an unknown to an established database is effective in establishing health status.

The following experimental data serve as a basis for this application. First, data from healthy human individuals shows that there is an oscillation pattern in the carbon isotope ratios when the data is decomposed and analyzed (FIG. 1). This oscillation pattern is independent of $CO_2$ concentration (FIG. 2) and machine noise (FIG. 3). Second, a mouse endotoxemia model was used to study changes in carbon isotope ratio oscillation due to infection (FIG. 4). When raw data from the mouse model was normalized and smoothed using a standard Savitzky-Golay filter (order=2) it is apparent that the oscillation patterns are nonlinear, but distinguishable visually between healthy and sick individuals (FIG. 5). Third, using another analysis method (Hilbert-Huang transformation), it is shown that the normalized and smooth data could be decomposed to visually provide embedded oscillatory patterns useful for analytical analysis (FIG. 6). Fourth, Fourier analyses of the decomposed oscillation data show an ability to distinguish infected animals from non-infected animals (FIG. 7). Fifth, using a difference analysis procedure where an individual's oscillation data was compared to known reference populations of healthy and infected populations, not only could the health status of the individual be determined, but environmental factors, such as diet, which are known to alter breath isotope rations did not interfere with the ability to distinguish infected from healthy in mice (FIGS. 8, 9, and 10).

The invention is further illustrated by the following non-limiting examples.

EXAMPLES

Experimental Protocol

Mouse studies: Mice were infected with a bacterial endotoxin (LPS), and the changes in stable isotope ratios in their breath were monitored via cavity ringdown spectroscopy, using a Picarro G2101-i Isotopic $CO_2$ analyzer and sampling every second. The endotoxin is a glycolipid component of the cell wall from gram-negative bacteria, which induces a strong inflammatory response known as the acute phase response, which is hallmark of infection. Measurements of isotopic ratios at concentrations of $CO_2$ ranging from 0.1% to 4% are typical in breath.

Eight-week-old male BALB/c mice were maintained on a 12 hour light/dark cycle, and allowed ad libitum access to food and water. Mice were randomly assigned one of three groups low (1 mg/kg) or high (5 mg/kg) lipopolysaccharide (LPS) or sham (saline) injection. Mice were placed serially in a metabolic chamber (one per day) at 9:45 am. Airflow through the chamber was maintained at a rate so that $CO_2$ concentrations did not exceed 0.5%. Carbon delta values (i.e. $^{13}CO_2/^{12}CO_2$ ratio) were measured continuously (i.e., about one data point per second) via a side stream using a Picarro G2101-i Isotopic $CO_2$ analyzer. At 11:45 AM mice received an intraperitoneal injection of lipopolysaccharide (LPS) at either 1 or 5 mg/kg body weight in saline or saline alone. Mice were removed from the chamber at the end of each day at 3:45 pm.

Example 1

Healthy Human Breath Exhibits Delta Oscillations

Healthy fasted humans were instructed to sit quietly at a desk while wearing a sealed mask. The mask consisted of an industrial volatile organic compound mask with all filters removed and a ¼ inch polyethylene tube connecting the mask to the $iCO_2$ analyzer. Exhaled air from the mask was mixed with $CO_2$ free air (Zero Air) so that the final $CO_2$ concentration was approximately 1000 ppm. Measurements were collected for at least 1 hour each day. Continuous data (sample/second) was obtained from the Picarro G2101-i Isotopic $CO_2$ analyzer. The data was smoothed using a standard Savitzky-Golay filter (order=2).

To verify the visual observation of oscillations, a Hilbert Huang transform was performed and the embedded oscillatory pattern (modes) were discerned by extracting other embedded oscillatory patterns. The first and the second mode represent the first and second extraction of oscillations with long oscillation periods (30 to 60 minutes) and were not used here. These longer cycle modes did not show discernible differences between healthy and sick based on the data from the current instrument. In addition, since the collection of repeated oscillatory cycles using long oscillation periods expanded the time necessary for evaluating patterns of oscillations (in other words, use of long oscillation patterns did not shorten the window to detect infection status over existing slope technology). The third and fourth extracted modes were superimposed and visually examined for the presence of oscillation. The results are demonstrated in FIG. 1. The sum of the modes 3 and 4 generated by a Hilbert-Huang transformation of smoothed oscillation data from a healthy human breath sample collected for 30 minutes (0.5 hr) is shown. Modes 3 and 4 were selected for additional analysis since they had oscillation periods that permitted 4 to 15 oscillations per hour, that is, modes 3 and 4 are functional oscillation patterns. This analysis shows that humans exhibit oscillation patterns in delta values. Each solid horizontal bar begins at a "first key" peak and continues to the subsequent "first key" peak. There are two "marker" peaks between each pair of key peaks. The triplet of peaks forms a repeating feature (or pattern). This peak-to-peak time is one oscillation period. The physical Y-axis approximately follows the scale of delta isotope approximately. The plot is scale-free because it is generated using the superposition of two modes of the Hilbert-Huang transform.

The possibility existed that the observed oscillations are an artifact of either the instrument, the background, the experimental set up, or the $CO_2$ production of humans (and mice) that exhibits oscillatory behavior. We tested the correlation between $CO_2$ levels and delta values (FIG. 2). As shown, the correlation is effectively zero, meaning that there is effectively no relationship between $CO_2$ oscillations and delta value oscillations.

Data was collected from background (chamber with no organism) and room data. The data exhibited minor variations (less than 0.5 ppm). The variations are not consistent with an oscillatory pattern and the amplitude is significantly smaller. (FIG. 3)

Considered together, the data demonstrate that: 1) oscillation of delta values are present in humans, and 2) they are not artifacts of the instrumentation or $CO_2$.

Example 2

Mouse Breath Exhibits Delta Oscillations that Change Post LPS Treatment

Continuously obtained data was first compared to previously collected data to insure that the established decreased (more positive) carbon isotope delta values upon LPS treatment have been preserved. This step acts as a control for the method of faster sampling and data processing. Specifically, a downtrend of isotope ratio post LPS has already been established through the use of previous instruments. The present instrument allows detection of the same downtrend for LPS-injected mice (FIG. 4). Compared to previous measurements where delta values were measured every 15 minutes, the data shown in FIG. 4 was taken using a new generation monitor of isotopes where delta values are measured every second. This figure demonstrates that the downward trend observed previously, could be observed when the new instrument is used. More importantly, the new data suggested that there were oscillation patterns in breath that might be useful in distinguishing control versus LPS injection. Data is for a period of approximately one hour with the first time point at injection=0 hours.

The data from FIG. 4 were examined next for the presence of oscillatory patterns as shown in FIG. 5. Data normalization was performed according to the steps defined in the section on data normalization below. One particular aspect of data normalization, the smoothing step, reduces the noise in the data background. The data was visually inspected for all mice for the presence of oscillatory pattern. Oscillatory patterns were present pre- and post-injection of LPS in all mice are as described in experiment 1 above.

Visual inspection of a close up after normalization and smoothing shows the presence of complex oscillations. Data is for a period of 15 minutes prior to LPS injection for all mice shown in the figure about the Horizontal axis: "scaled time", and vertical axis: isotope delta ratio.

Because this data contains a complex oscillatory pattern that seemed to combine multiple modes, a Hilbert-Huang transform was applied to decouple these modes. The decoupled modes further illustrated the presence of oscillations. Specifically, a total of seven modes were decoupled and 2 modes where selected as functional oscillation patterns based on the presence of 4 to 15 oscillations per hour for further analysis by Fourier methods. FIG. 6 shows the selected modes for 6 mice. These two modes exhibited significantly altered behavior pre- and post LPS. Standard computational algorithms for classification would be able to separate these oscillatory patterns according to the state of the organism (healthy, LPS, etc.)

FIG. 7 is a Fourier analysis of a "30 minute" segment of the frequency modes of 4 to 15 cycles per hour generated by a Hilbert-Huang transformation (of normalized oscillation data) for a healthy and LPS-injected mouse. The X-axis is normalized and arbitrary, where the frequency of oscillations per unit time increase with increasing scale. The Y-axis is the transform of the scale-free Hilbert-Huang y-axis. The approximate frequency for the healthy mouse is 7 minutes. The LPS-injected mouse has a split frequency plus a lower frequency appearing at 10 minutes.

This analysis shows that organisms in healthy state have at least one functional oscillation frequency with numerous less dominant frequencies. In the case of the mouse above, there is a functional oscillation frequency at approximately 7 minutes when the mouse is healthy. When perturbed by LPS, the functional oscillation frequency of seven minutes splits, and a lower frequency, a modified oscillation frequency, (10 minutes, for example) appears. This is a strong indicator of disruption to homeostasis that appears very shortly after LPS injection. With the current analysis, each organism (a phenotype) presents its own model, with its own "noise" in the observed data. The Hilbert-Huang, being nonlinear, is not frequency selective—it is mode selective and when coupled with Fourier analysis is useful in the detection of changes in animal health.

Example 3

Alternative Analysis Using Time Series Classification

Next, the sick and healthy organisms (including diet variations) were analyzed and classified using a different method. The use of this alternative approach suggested that a) this oscillation data, despite-natural variability in observed data, clearly separates the healthy from the sick, and b) the method of analysis is less important and other methods known in the art may be used. The fundamental observation that oscillations are present and they change in a manner that can be detected is the more important point.

The protocol established herein builds on a collection of algorithms generally designed for time series classification. Time series classification is a supervised learning approach aimed at labeling temporally structured data of possibly varying length. A number of applications have been naturally cast into the form of time series classification. For example, indexing of ECG diagrams in medical diagnosis is an example of a similar application. Portions of the protocol use algorithms that are similar in concept. However, the overall protocol differs in several application-specific ways, which is adapted to the nature of our approach to diagnosis.

In establishing the protocol for data analysis, the following diagnostic scenarios were taken into consideration. Monitoring of a sick patient or a sick organism can commence at any time. At the commencement of monitoring, the target animal or patient may be healthy or sick. If the target is sick, the length of time since the target has been sick is not generally known. The goal is to collect data for a short period of time from the target and decide if the target is sick or healthy. This scenario does not preclude the collection of longer periods of data or extended continuous monitoring. The short time window establishes a threshold time (minimum time) for diagnosis. Longer times can improve the sensitivity of the diagnostic test.

Having established the presence of oscillatory trends in the isotope ratios, an analytical procedure for the identification and classification of ratios with different oscillatory patterns was defined.

To preserve the clarity of presentation, the discussion of the data will proceed with the implicit assumption that data from the instrument is being used in raw form. The necessary statements regarding the details of transformations of the data are made in the description of the algorithm. These transformations will not impact the methodology or procedure described in the forgoing steps. The existing data from the mice can be represented as a set of time series annotated with a label: $D_l = \{(x_k, i_k) \in X \times I\}$. In this set, X are time series (vectors), and i is a label indicating the state of organism—for example, sick or healthy. The label l for the set is used to indicate index for the alternate sets that can be used to distinguish various states of an organism. The time series vectors consist of isotope ratio values collected over a time span longer than a prescribed period and sampled at a sufficient rate. An example of time period is 35 minutes, and an example of sampling rate is once every 30 seconds. An initial set is used for the purpose of constructing an estimator $f$. The function $f$ evaluates values of new time series vectors (future) by suggesting how they differ from a baseline set. Specifically, as an example, given a future data set y of prescribed length, the estimators $f(y)$ will provide a value for sick (or healthy) along with a given probability p (1-p for healthy). FIG. 8 is identical to FIG. 4. For each simulation run a set of 30 minute windows was randomly selected (using a pseudo-random number generator). The set of black boxes in FIG. 8 shows one realization of this random selection (all windows are not shown for clarity—otherwise the figure would be covered with black windows).

Once $f$ has been constructed, the evaluation of the state of an organism based on a new time series vector y is straightforward $-f(y)$ provides the state with probability p. When $f(y)$ changes (probability p is diminished below a threshold, for example), then a state change in an organism has occurred. Although straightforward in concept, the algorithm in practice utilizes a series of pre-processing steps. These steps are discussed below.

---

Algorithm: pre process data (used for learning $f$ as well as computing $f(y)$)
  Input: x ; output x   % a new vector of the same size as x
  Smooth x   % smoothing kernel is applied to raw data
  Transform x   % a spectral transform of x - for example Fourier
  Phase x   % phase of the signal is adjusted to a reference phase

---

The pre-processed data is the basis for constructing the computational function $f$. We refer to this generically as f—although, by construction, the results is a stratified ensemble of functions that evaluate $f$ at a given vector y at multiple thresholds in order to obtain the probabilities.

---

Algorithm: learn $f$
  Input: the set of signals and classes {x,i} ; ouput: $f$
  Pre process all data {x}
  Assemble $D_I \equiv \{(x_k, i_k) \in X \times I\}$
  Solve the following optimization problem (see below for algorithm).
  Minimize $D[f] = \Sigma_{Card(\{x\})} |i_k - f(x_k)|p_\epsilon - \lambda ||f||_{p_\epsilon}$
  Save the results as the definition of $f$

---

FIG. 9 shows a lower dimensional projection of the time series as points on a 2D plane. The estimator $f$ works on the time series data which is 70-dimensional. The probabilities are generated by using numerous estimators using alternative random window samplings of the data. Sampled runs are maintained for subsequent cross-validation.

The decision function uses the construction $f$ to evaluate any new time series y. The output assigns a weight (probability) to each (binary) state. We note that in continuous measurements the running probability value can be used to ascertain gradual state changes.

---

Algorithm: Decide y
  Input: y,$f$ ; output: p,i
  Apply p,I = $f(y)$;

---

In FIG. 10, an experiment was conducted where mice were fed two diets with dissimilar isotope ratios. Breath isotope oscillation patterns were measured. Using the algorithm for problem solving shown, data from mice fed each diet were blended and tested to discern if these healthy mice could be distinguished from mice injected with endotoxin (sick). As would be predicted the blended data from mice fed the different diets did scale without dietary isotope levels (intermediate between the healthy breath of mice fed their respective diets), but was clearly distinct from sick mice. These data confirmed that diet was not a confounding factor in distinguishing health of individuals based on the oscillation pattern of breath isotopes.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of determining if an individual is transitioning from a healthy state to an unhealthy state, the method comprising:
    monitoring breath taken from the individual and measuring a relative amount of a first isotope to a second isotope therein over a total time interval ($t_{total}$), wherein the individual is healthy during the time interval $t_{0\text{-}healthy}$, wherein $t_0$ is a time point at the start of time interval $t_{total}$, and $t_{healthy}$ is time point during $t_{total}$ in which the individual is healthy, identifying a healthy functional oscillation pattern in the relative amount of the first isotope to the second isotope therein during time interval $t_{0\text{-}healthy}$, identifying a test functional oscillation pattern in the relative amount of the first isotope to the second isotope therein a test time interval $t_{test}$ within $t_{total}$, wherein $t_{test}$ does not overlap $t_{0\text{-}healthy}$, and determining that the individual is transitioning from a healthy state to an unhealthy state when the healthy functional oscillation pattern and the test functional oscillation pattern are distinct in period of oscillation, oscillations per unit time, and/or variability in oscillation period, wherein the first and second isotopes are selected from the group consisting of a pair of $^{13}C$ and $^{12}C$, a pair of $^{15}N$ and $^{14}N$, a pair of $^{17}O$ and $^{16}O$, and a pair of sulphur isotopes.

2. The method of claim 1, further comprising determining a slope by determining the change in the relative amount of the first isotope to the second isotope changes from time $t_0$ to time $t_x$ within time period $t_{total}$.

3. The method of claim 1, wherein the healthy functional oscillatory pattern is independent of the diet of the individual.

4. The method of claim 1, wherein the first and second isotopes are the pair of $^{13}C$ and $^{12}C$.

5. The method of claim 1, wherein the monitoring step uses cavity ringdown spectroscopy to determine the changes in the relative amount of the first isotope to the second isotope.

6. The method of claim 1, wherein the period of oscillation, oscillations per unit time, and/or variability in oscillation period and/or oscillations per unit in time of the healthy functional oscillation pattern differs by more than 10% from the test functional oscillation pattern when the individual transitions from a healthy state to an unhealthy state.

7. The method of claim 1, wherein the time interval $t_{total}$ is at least 5 minutes and includes at least one interval from a healthy state and at least one interval from an unhealthy state.

8. The method of claim 1, wherein measuring a relative amount of the first isotope to the second isotope therein over a time interval $t_{total}$ includes continuous measurement or measurement over discrete time intervals ($t_i$) within the time interval $t_{total}$.

9. The method of claim 1, wherein the healthy functional oscillatory pattern in the relative amount of the first isotope to the second isotope has a period of oscillation of 6 to 7 minutes and 8.5 to 10 oscillations per hour.

10. The method of claim 1, wherein identifying the healthy functional oscillation pattern in the relative amount of the first isotope to the second isotope therein over the time interval $t_{0\text{-}healthy}$ comprises decomposing the relative amount of the first isotope to the second isotope therein over the time interval $t_{0\text{-}healthy}$ to produce a finite number of intrinsic modes, wherein the first dominant oscillation mode is one of the intrinsic modes.

11. The method of claim 10, further comprising identifying high frequency oscillation modes using mode decomposition, and filtering the high frequency oscillation modes from the relative amount of the first isotope to the second isotope therein over the time interval $t_{0\text{-}healthy}$.

12. The method of claim 1, further comprising identifying a second healthy functional oscillation period in the relative amount of the first isotope to the second isotope therein over the time period ($t_{0\text{-}healthy}$).

13. The method of claim 1, wherein the individual is an isotopically unenriched individual.

14. The method of claim 1, wherein the individual is intubated.

15. A method of determining whether an individual is in an unhealthy state, the method comprising:

monitoring breath taken from the individual and measuring a relative amount of a first isotope to a second isotope therein over a total time interval ($t_{total}$), wherein the individual is unhealthy during the time interval $t_{0\text{-}unhealthy}$, wherein $t_0$ is a time point at the start of time interval $t_{total}$, and $t_{unhealthy}$ is time point during $t_{total}$ in which the individual is unhealthy, identifying an unhealthy functional oscillation pattern in the relative amount of the first isotope to the second isotope therein during time interval $t_{0\text{-}unhealthy}$, identifying a test functional oscillation pattern in the relative amount of the first isotope to the second isotope therein a test time interval $t_{test}$ within $t_{total}$, wherein $t_{test}$ does not overlap $t_{0\text{-}unhealthy}$, and determining that the individual is transitioning from an unhealthy state to a healthy state when the unhealthy functional oscillation pattern and the test functional oscillation pattern are distinct in period of oscillation, oscillations per unit time, and/or variability in oscillation period, wherein the first and second isotopes are selected from the group consisting of a pair of $^{13}C$ and $^{12}C$, a pair of $^{15}N$ and $^{14}N$, a pair of $^{17}O$ and $^{16}O$, and a pair of sulphur isotopes.

16. The method of claim 15, further comprising determining a slope by determining the change in the relative amount of the first isotope to the second isotope changes from time $t_0$ to time $t_x$ within time period $t_{total}$.

17. The method of claim 15, wherein the unhealthy functional oscillation pattern is independent of the diet of the individual.

18. The method of claim 15, wherein the first and second isotopes are the pair of $^{13}C$ and $^{12}C$.

19. The method of claim 15, wherein the monitoring step uses cavity ringdown spectroscopy to determine the changes in the relative amount.

20. The method of claim 15, wherein the period of oscillation, oscillations per unit time, and/or variability in oscillation period and/or oscillations per unit in time of the healthy functional oscillation pattern differs by more than 10% from the test functional oscillation pattern when the individual transitions from a healthy state to an unhealthy state.

21. The method of claim 15, wherein the time interval $t_{total}$ is at least 5 minutes.

22. The method of claim 15, wherein measuring a relative amount of the first isotope to the second isotope therein over a time interval $t_{total}$ includes continuous measurement or measurement over discrete time intervals ($t_i$) within the time interval $t_{total}$.

23. A method of determining the severity of an infection in an individual, the method comprising:

monitoring breath taken from the individual and measuring a relative amount of a first isotope to a second isotope therein over a time period (t), wherein the first and second isotopes are selected from the group consisting of a pair of $^{13}C$ and $^{12}C$, a pair of $^{15}N$ and $^{14}N$, a pair of $^{17}O$ and $^{16}O$, and a pair of sulphur isotopes;

identifying for the individual a functional oscillation pattern in the relative amount of the first isotope to the second isotope therein over the time period (t), and determining any differences between the functional oscillation pattern for the individual compared to an average functional oscillation pattern for a healthy and/or infected reference population, wherein the degree of difference between the functional oscillation pattern for the individual and the average functional oscillation pattern for the reference populations determines the severity of the infection.

24. The method of claim 23, wherein the functional oscillation pattern for the individual is independent of the diet of the individual.

25. The method of claim 23, wherein the first and second isotopes are the pair of $^{13}C$ and $^{12}C$.

26. The method of claim 23, wherein the monitoring step uses cavity ringdown spectroscopy to determine the changes in the relative amount.

27. The method of claim 23, wherein the time period is at least 5 minutes.

28. The method of claim 23, wherein measuring a relative amount of the first isotope to the second isotope therein over a time period (t) includes continuous measurement or measurement over discrete time intervals ($t_i$) within the time period (t).

29. A method of determining whether an individual is in an unhealthy state, the method comprising
monitoring breath taken from the individual and measuring a relative amount of a first isotope to a second isotope therein over a time period ($t_{total}$), wherein the first and second isotopes are selected from the group consisting of a pair of $^{13}C$ and $^{12}C$, a pair of $^{15}N$ and $^{14}N$, a pair of $^{17}O$ and $^{16}O$, and a pair of sulphur isotopes,
identifying a functional oscillation pattern in the relative amount of the first isotope to the second isotope therein over the time period ($t_{total}$), and comparing the functional oscillation pattern for the individual with a functional oscillation pattern averaged across a known healthy and/or unhealthy reference population, and
determining that the individual is in an unhealthy state when the functional oscillation pattern for the individual is different in frequency and/or amplitude to the averaged functional oscillation pattern for the healthy and/or infected reference population.

\* \* \* \* \*

UNITED STATES PATENT AND TRADEMARK OFFICE
CERTIFICATE OF CORRECTION

PATENT NO.       : 8,512,676 B1
APPLICATION NO.  : 13/414061
DATED            : August 20, 2013
INVENTOR(S)      : Eghbalnia et al.

Page 1 of 1

It is certified that error appears in the above-identified patent and that said Letters Patent is hereby corrected as shown below:

On the title page item [54] and in the specification, column 1, line 3, Title, delete "ATHWAYS", and insert --PATHWAYS--

Signed and Sealed this
Fifteenth Day of October, 2013

Teresa Stanek Rea
*Deputy Director of the United States Patent and Trademark Office*